United States Patent
Shimizu

(10) Patent No.: US 7,983,865 B2
(45) Date of Patent: Jul. 19, 2011

(54) POWER SUPPLY APPARATUS FOR OPERATION AND RESONANT FREQUENCY SEARCHING METHOD

(75) Inventor: Koh Shimizu, Kodaira (JP)

(73) Assignee: Olympus Medical Systems Corp. (JP)

( * ) Notice: Subject to any disclaimer, the term of this patent is extended or adjusted under 35 U.S.C. 154(b) by 594 days.

(21) Appl. No.: 12/103,070

(22) Filed: Apr. 15, 2008

(65) Prior Publication Data

US 2009/0259423 A1    Oct. 15, 2009

(51) Int. Cl.
*G01R 23/00* (2006.01)
*G06F 13/14* (2006.01)

(52) U.S. Cl. .................. 702/75; 601/2; 702/60
(58) Field of Classification Search .......... 702/65, 702/72, 75, 78, 117, 60; 601/2; 606/69, 606/170, 180
See application file for complete search history.

(56) References Cited

U.S. PATENT DOCUMENTS

| 4,966,131 | A | * | 10/1990 | Houghton et al. ............ 601/2 |
| 6,662,127 | B2 | | 12/2003 | Wiener et al. |
| 6,898,536 | B2 | | 5/2005 | Wiener et al. |

FOREIGN PATENT DOCUMENTS

| JP | 2002-45368 | 2/2002 |
| JP | 2004-216107 | 8/2004 |
| JP | 2005-253874 | 9/2005 |
| JP | 2006-231084 | 9/2006 |

* cited by examiner

*Primary Examiner* — John H Le
(74) *Attorney, Agent, or Firm* — Ostrolenk Faber LLP

(57) ABSTRACT

A power supply apparatus for operation supplies a drive signal of a resonant frequency to a surgical instrument to drive the instrument. A recognition section recognizes a surgical instrument connected to the power supply apparatus. A setting section sets a frequency scanning condition according to the surgical instrument recognized by the recognition section. A scanning section scans for the resonant frequency of the surgical instrument on the basis of the frequency scanning condition set by the setting section.

14 Claims, 6 Drawing Sheets

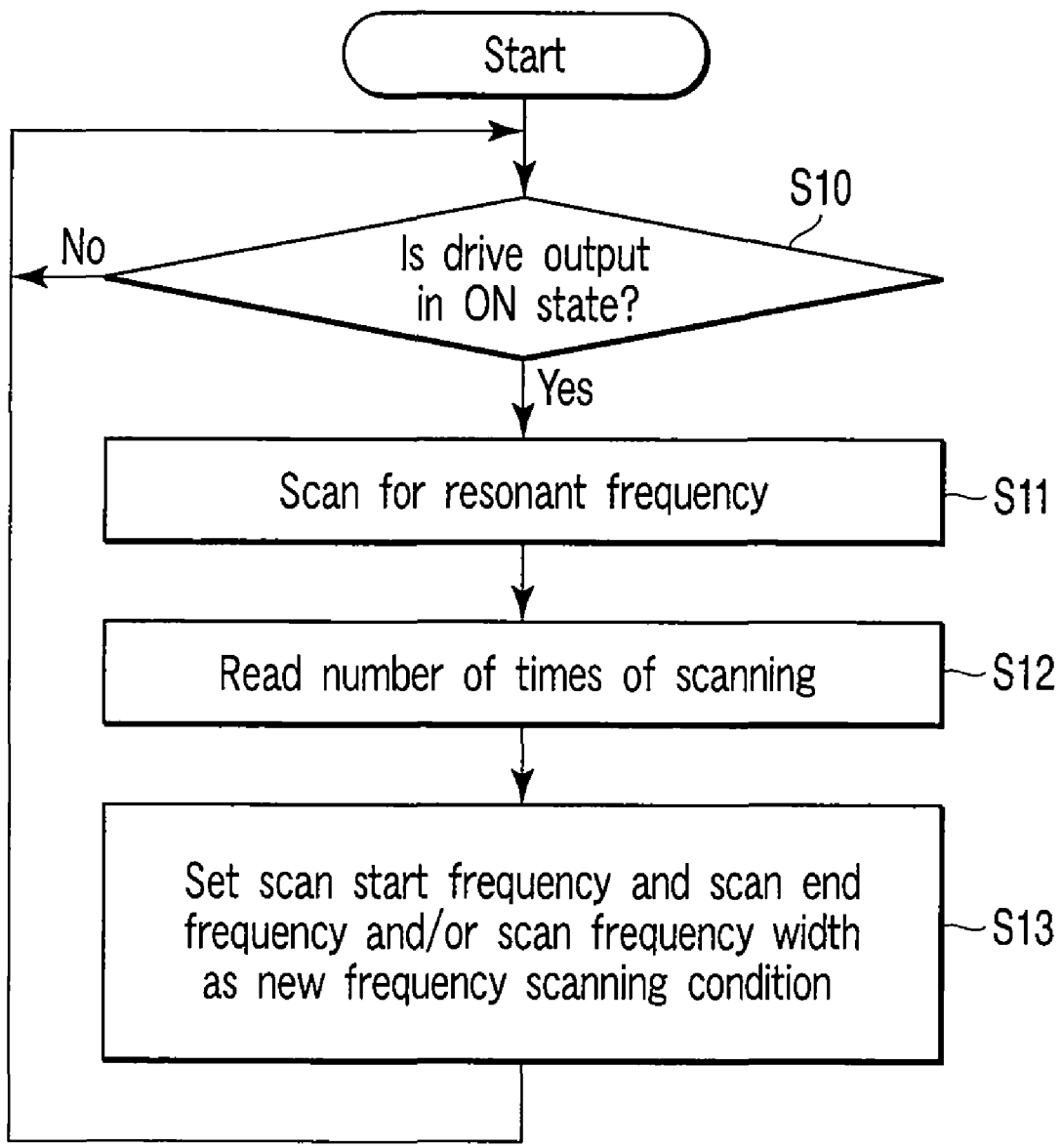
F I G. 8

POWER SUPPLY APPARATUS FOR OPERATION AND RESONANT FREQUENCY SEARCHING METHOD

BACKGROUND OF THE INVENTION

1. Field of the Invention

The present invention relates to a power supply apparatus for operation and a resonant frequency searching method.

2. Description of the Related Art

In Jpn. Pat. Appln. KOKAI Publication No. 2002-45368, an ulltrasonic coagulation/incision apparatus provided with resonant frequency follow-up means for following up a resonant frequency for driving an ultrasonic vibrator is disclosed. In Jpn. Pat. Appln. KOKAI Publication No. 2004-216107, an ultrasonic operation apparatus provided with frequency control means for controlling an oscillating frequency on the basis of phase information on a drive signal supplied to an ultrasonic vibrator is disclosed. In Jpn. Pat. Appln. KOKAI Publication No. 2005-253874, an ultrasonic surgical instrument provided with a gripping section, insertion section, vibrator mounting section, and vibrator is disclosed. In Jpn. Pat. Appln. KOKAI Publication No. 2006-231084, a control method of an ultrasonic operation system in which a handpiece including an ultrasonic vibrator, and an apparatus main body including oscillation means for generating a drive signal for driving the ultrasonic vibrator are detachably connected to each other is disclosed. Further, in U.S. Pat. No. 6,898,536, a method of improving a start-up of an ultrasonic system in a zero-load state is disclosed. In U.S. Pat. No. 6,662,127, a method of detecting existence of a blade in an ultrasonic system is disclosed.

BRIEF SUMMARY OF THE INVENTION

According to a first aspect of the present invention, there is provided a power supply apparatus for operation for supplying a drive signal of a resonant frequency to a surgical instrument to drive the instrument comprising:

a recognition section for recognizing a surgical instrument connected to the power supply apparatus;

a setting section for setting a frequency scanning condition according to the surgical instrument recognized by the recognition section; and a scanning section for scanning for the resonant frequency of the surgical instrument on the basis of the frequency scanning condition set by the setting section.

According to a second aspect of the present invention, there is provided a power supply apparatus for operation for supplying a drive signal of a resonant frequency to a surgical instrument to drive the instrument comprising:

a count section for counting the number of times the resonant frequency of the surgical instrument is scanned for;

a setting section for setting a frequency scanning condition according to the number of times of the scanning counted by the count section; and a scanning section for scanning for the resonant frequency of the surgical instrument on the basis of the frequency scanning condition set by the setting section.

According to a third aspect of the present invention, there is provided a power supply apparatus for operation for supplying a drive signal of a resonant frequency to a surgical instrument to drive the instrument comprising:

a measurement section for measuring a capacitance component of the surgical instrument on the basis of a voltage, a current, and impedance detected from the drive signal supplied to the surgical instrument;

a setting section for setting a frequency scanning condition according to the capacitance component measured by the measurement section; and a scanning section for scanning for the resonant frequency of the surgical instrument on the basis of the frequency scanning condition set by the setting section.

According to a fourth aspect of the present invention, there is provided a method of scanning for a resonant frequency of a surgical instrument, comprising:

a recognition step of recognizing the surgical instrument;

a setting step of setting a frequency scanning condition according to the surgical instrument recognized in the recognition step; and a scanning step of scanning for the resonant frequency of the surgical instrument on the basis of the frequency scanning condition set in the setting step.

According to a fifth aspect of the present invention, there is provided a method of scanning for a resonant frequency of a surgical instrument, comprising:

a counting step of counting the number of times the resonant frequency of the surgical instrument is scanned for;

a setting step of setting a frequency scanning condition according to the number of times of the scanning counted in the counting step; and a scanning step of scanning for the resonant frequency of the surgical instrument on the basis of the frequency scanning condition set in the setting step.

According to a sixth aspect of the present invention, there is provided a method of scanning for a resonant frequency of a surgical instrument, comprising:

a measurement step of measuring a capacitance component of the surgical instrument on the basis of a voltage, a current, and impedance detected from a drive signal supplied to the surgical instrument;

a setting step of setting a frequency scanning condition according to the capacitance component measured in the measurement step; and a scanning step of scanning for the resonant frequency of the surgical instrument on the basis of the frequency scanning condition set in the setting step.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 8 is a flowchart for explaining a method of scanning for a resonant frequency of a hand-piece according to a second embodiment of the present invention.

Figure 10:
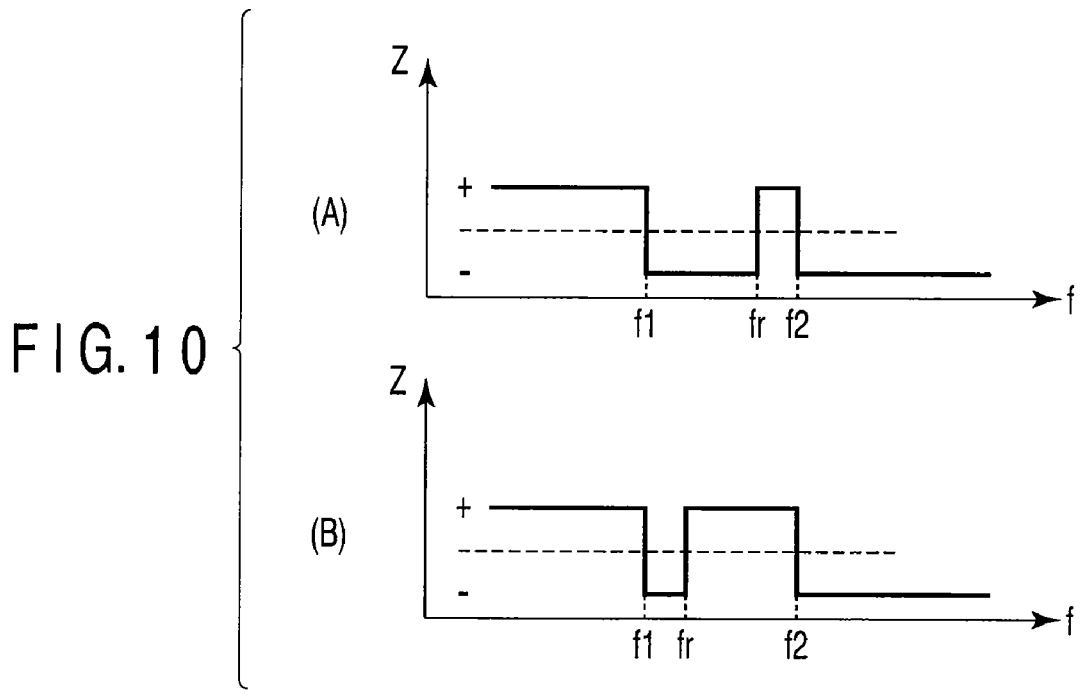

(A) and (B) in FIG. 10 are views showing two phase frequency characteristics corresponding to amounts of capacitance components of ultrasonic vibrators.

DETAILED DESCRIPTION OF THE INVENTION

Figure 1:
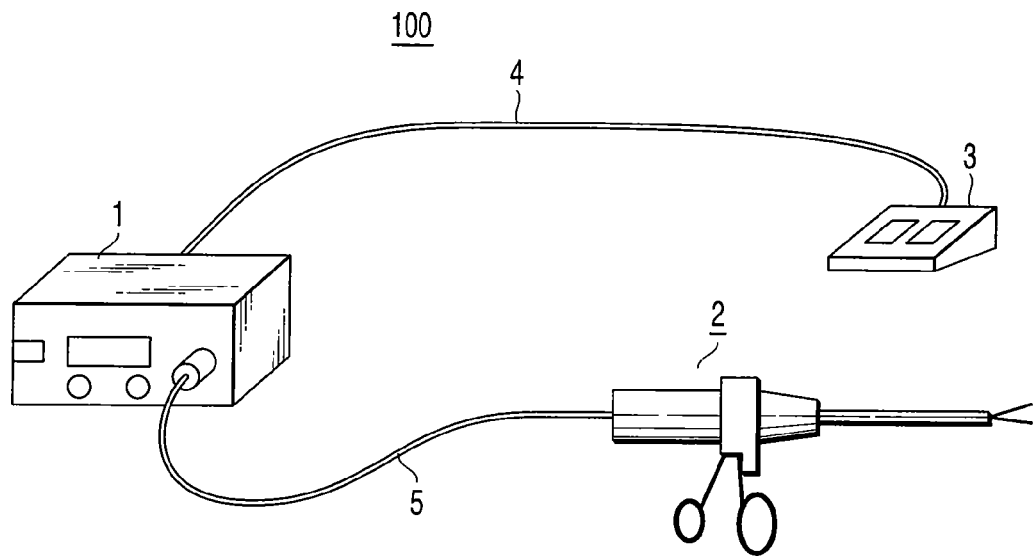
FIG. 1 is an external perspective view of an ultrasonic operation system.

Embodiments of the present invention will be described below in detail with reference to the accompanying drawings. An endoscopic surgical operation for performing medical treatment of a diseased part to be performed by using a scope for observing a state in an abdominal cavity of a patient is known. FIG. 1 is an external perspective view of an ultrasonic operation system used as an example of a system for such an endoscopic surgical operation. The ultrasonic operation system is constituted of an ultrasonic power source unit 1 serving as a power supply apparatus for operation for generating an ultrasonic output for driving an ultrasonic vibrator, a hand-piece 2 serving as an ultrasonic surgical instrument for performing treatment by using an ultrasonic output supplied from the ultrasonic power source unit 1 through a cable 5, and a foot switch 3 connected to the ultrasonic power source unit 1 through a cable 4, for controlling the ultrasonic output from the ultrasonic power source unit 1.

Figure 2:
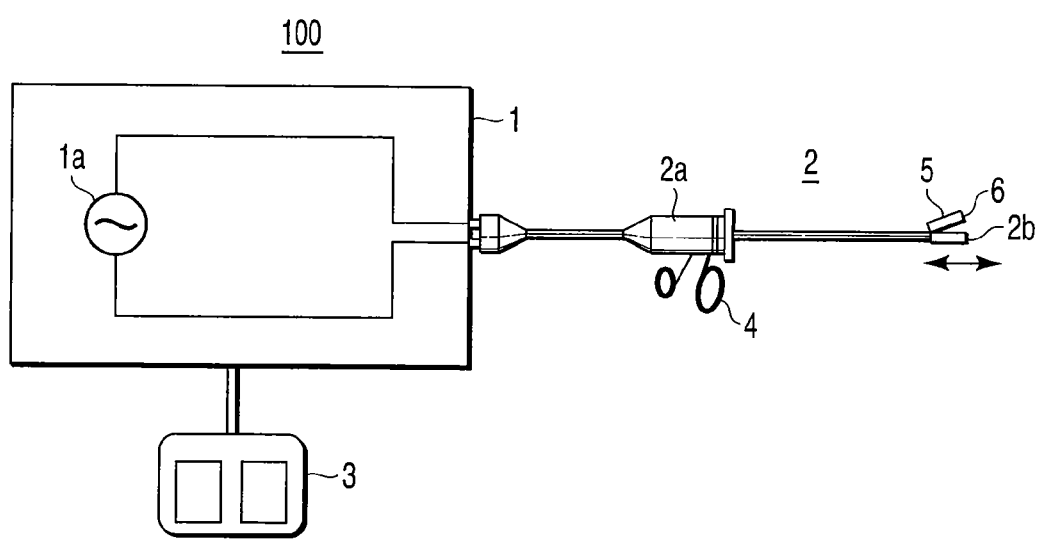
FIG. 2 is a view showing a schematic configuration of the ultrasonic operation system.

FIG. 2 is a view showing a schematic configuration of the ultrasonic operation system. The hand-piece 2 is constituted of a hand-piece main body section 2a which includes handles 4, and in which an ultrasonic vibrator (not shown) is incorporated, and a probe 2b for transmitting vibration of the ultrasonic vibrator to a treatment section 5. The ultrasonic power source unit 1 is provided with an ultrasonic oscillator circuit 1a for generating electric energy for vibrating the ultrasonic vibrator. An electric signal output from the ultrasonic power source unit 1 is converted into mechanical vibration (ultrasonic vibration) by the ultrasonic vibrator inside the hand-piece main body section 2a, and thereafter the vibration is transmitted by the probe 2b to the treatment section 5. The treatment section 5 is provided with a grasping section 6 called a jaw driven to be opened or closed with respect to the distal end of the probe 2b. When the handles 4 are operated, the grasping section 6 is driven to be opened or closed with respect to the distal end of the probe 2b, and coagulation or incision of living tissue is performed by utilizing frictional heat generated by holding the living tissue between the distal end of the probe 2b and the grasping section 6 and applying the ultrasonic vibration thereto.

Figure 3:
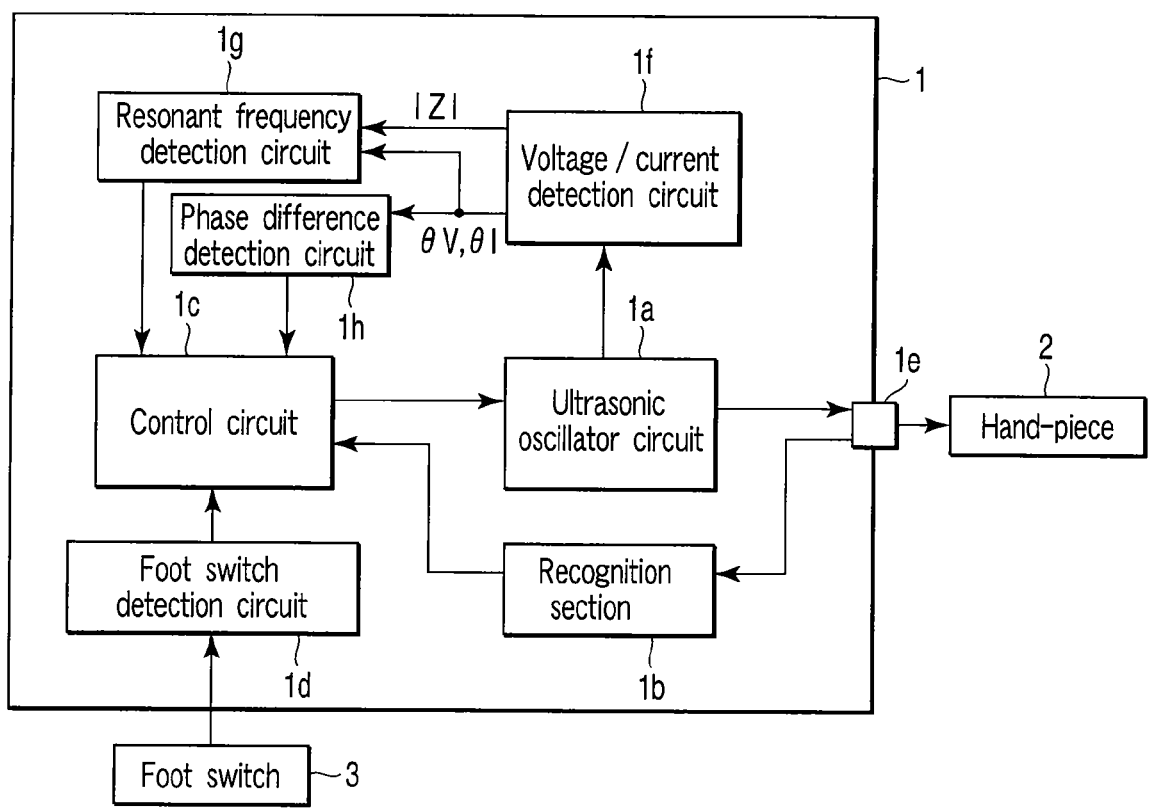
FIG. 3 is a functional block diagram for explaining a function of each unit in an ultrasonic power source unit in an ultrasonic operation system.

FIG. 3 is a functional block diagram for explaining a function of each unit in an ultrasonic power source unit in an ultrasonic operation system. The hand-piece 2 is connected to the ultrasonic power source unit 1 through a connector 1e. In the ultrasonic power source unit 1, an ultrasonic oscillator circuit 1a, voltage/current detection circuit 1f, resonant frequency detection circuit 1g, phase difference detection circuit 1h, foot switch detection circuit 1d, recognition section 1b, and control circuit 1c are provided. The ultrasonic oscillator circuit 1a is a part for generating a drive signal for driving the ultrasonic vibrator inside the hand-piece 2. The voltage/current detection circuit 1f is a part for detecting a voltage phase signal θV, a current phase signal θI corresponding to the vibration, and the impedance Z from the drive signal supplied to the ultrasonic vibrator. The phase difference detection circuit 1h is a part for detecting a phase difference between the detected phase of the voltage V and the detected phase of the current I. The resonant frequency detection circuit 1g is a part for detecting the resonant frequency of the ultrasonic vibrator on the basis of the voltage phase signal θV, the current phase signal θI, and the impedance Z which are output from the voltage/current detection circuit 1f. The foot switch detection circuit 1d is a part for detecting that the foot switch 3 has been operated by the operator. The recognition section 1b is a part for, when the hand-piece 2 is connected to the ultrasonic power source unit 1, reading a resistance value of a resistor incorporated in the hand-piece 2, and recognizing the type of the hand-piece 2. Examples of the hand-piece are an ultrasonic coagulation incision hand-piece, ultrasonic suction hand-piece, and the like.

Figure 4:
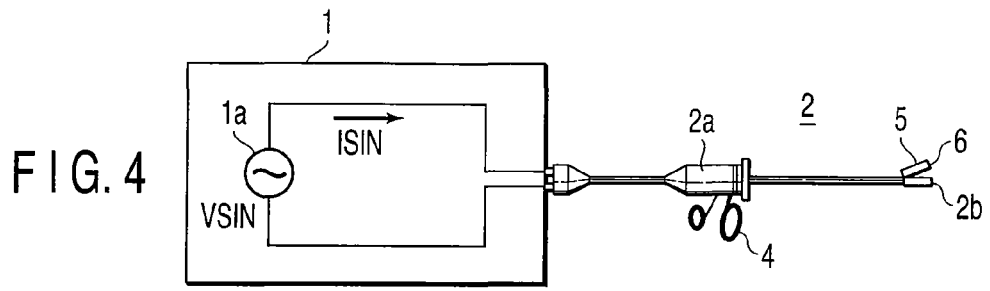
FIG. 4 is a view showing a state where a drive current generated in an ultrasonic power source unit flows to the hand-piece side.
Figure 5:
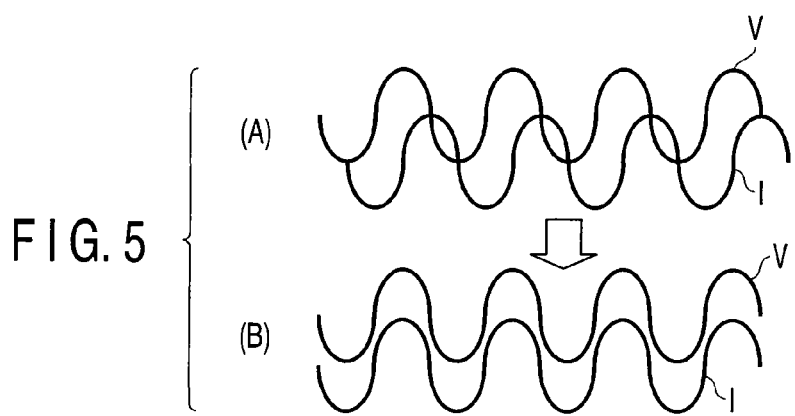
FIG. 5 is a view showing a relationship between a voltage phase and a current phase.
Figure 6:
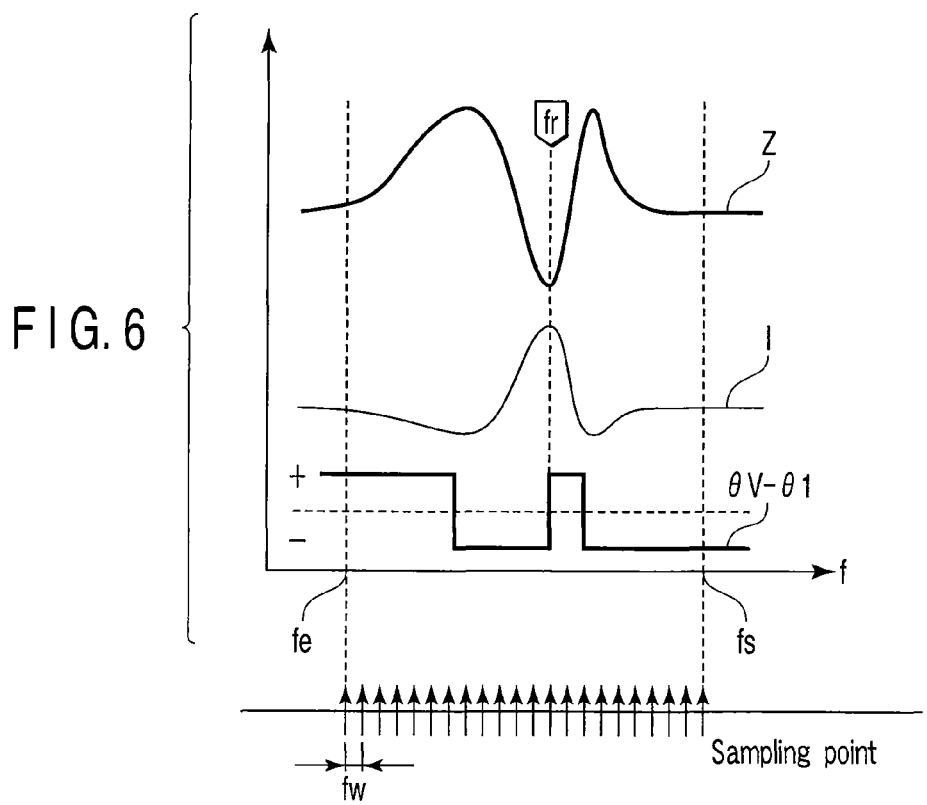
FIG. 6 is a view for explaining a procedure for scanning for a resonant frequency fr.

FIGS. 4 to 6 are views for explaining a control method of the ultrasonic drive in an ultrasonic operation system. In FIG. 4, in the ultrasonic oscillator circuit 1a, a sinusoidal drive voltage VSIN is generated. When a sinusoidal drive current ISIN corresponding to the voltage VSIN flows through the ultrasonic vibrator inside the hand-piece main body section 2a, the ultrasonic vibrator converts the electric signal into mechanical vibration, and transmits the vibration to the distal end of the probe 2b.

In the ultrasonic drive described above, when the ultrasonic wave is output at a constant oscillating frequency, a phase difference is produced between the voltage V and the current I as shown in FIG. 5(A), and hence the drive efficiency is lowered. Thus, the control circuit 1c in FIG. 3 drives the ultrasonic vibrator while searching for a resonance point at which the phase difference between the voltage V and the current I becomes 0 (FIG. 5(B)).

For example, in FIG. 6, the abscissa indicates frequency f, and the ordinate indicates impedance Z, current I, and phase difference (θV−θI). The part (θVθθI) indicates the phase difference. In this embodiment, a point at which the impedance Z is minimized is scanned for while the frequency is successively changed so as to detect the resonant frequency fr at which the phase difference (θV−θI) becomes zero. The control circuit 1c starts to drive the ultrasonic vibrator at the detected resonant frequency fr.

FIRST EMBODIMENT

Figure 7:
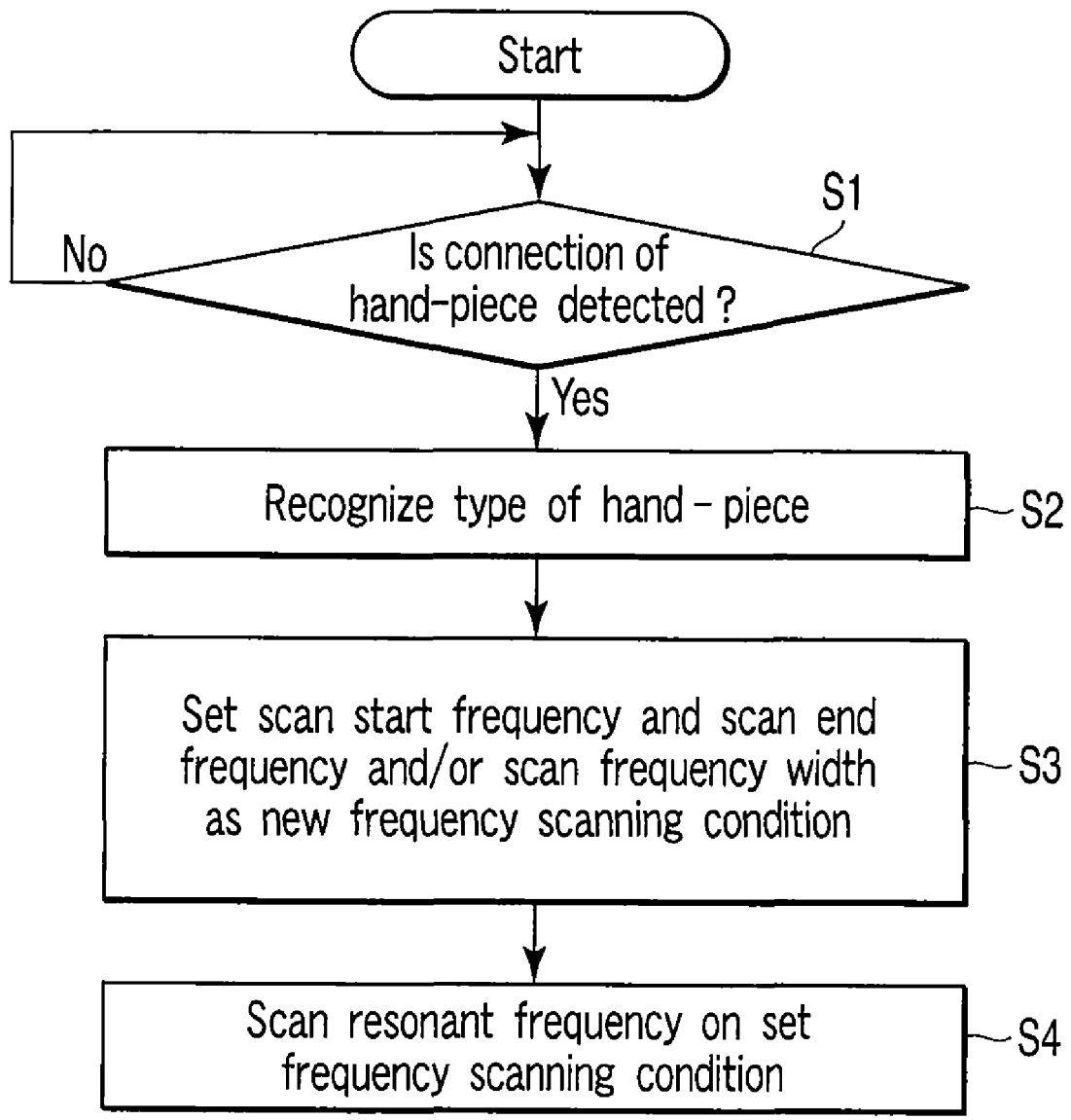
FIG. 7 is a flowchart for explaining a method of scanning for a resonant frequency of a hand-piece according to a first embodiment of the present invention.

FIG. 7 is a flowchart for explaining a method of scanning for a resonant frequency of a hand-piece according to a first embodiment of the present invention. First, a control circuit 1c judges whether or not a hand-piece 2 is connected to an ultrasonic power source unit 1 (step S1). When the hand-piece 2 is not connected to the ultrasonic power source unit 1, the control circuit 1c waits till the judgment result becomes YES. When the connection of the hand-piece to the power source unit 1 is confirmed, a recognition section 1b in FIG. 3 reads a resistance value of a resistor incorporated in the hand-piece 2, recognizes the type of the hand-piece 2 (step S2), and sends the recognition result to the control circuit 1c. The control circuit 1c includes therein a table in which the type of the hand-piece, scan start frequency, scan end frequency, and scan frequency width are made to correspond to each other. The control circuit 1c refers to this table to set at least one of (1) the scan start frequency and scan end frequency, and (2)

the scan frequency width as a new frequency scanning condition (step S3). In terms of the example of FIG. 6, fs is the scan start frequency, fe is the scan end frequency, and fw is the scan frequency width. Here, fw is the interval between two sampling points.

The control circuit 1c starts to scan for the resonant frequency on the set frequency scanning condition (step S4). According to the first embodiment described above, the frequency scanning condition is changed according to the type of the device, and hence it is possible to shorten the time needed for the resonant frequency scanning, and thus finally shorten the operation time needed to treat the living tissue.

SECOND EMBODIMENT

FIG. 8 is a flowchart for explaining a method of scanning for a resonant frequency of a hand-piece 2 according to a second embodiment of the present invention. First, a control circuit 1c judges whether or not a drive output for driving the hand-piece 2 is in the ON state (step S10). If the judgment result is NO, the control circuit 1c waits till the judgment result becomes YES. When it is confirmed that the drive output is in the ON state, the control circuit 1c executes the scanning in search of the resonant frequency on a preset frequency scanning condition (step S11). If the resonant frequency cannot be scanned for by one time scanning, the scanning is further executed. At this time, the number of times of the scanning operation is counted, and the counted result is stored in the internal memory of the control circuit 1c as the number of times of the scanning. If the resonant frequency cannot be scanned for after the scanning is executed the predetermined number of times, the control circuit 1c reads the number of times of the scanning from the memory (step S12). The control circuit 1c includes therein a table in which the number of times of the scanning, scan start frequency, scan end frequency, and scan frequency width are made to correspond to each other. The control circuit 1c refers to this table to set at least one of (1) the scan start frequency and scan end frequency, and (2) the scan frequency width as a new frequency scanning condition (step S13). In terms of the example of FIG. 6, fs is the scan start frequency, fe is the scan end frequency, and fw is the scan frequency width. Here, fw is the interval between two sampling points.

Then, the control circuit 1c returns to step S10, repeats the above steps until the resonant frequency is detected, and stops the scanning operation when the resonant frequency is detected. Incidentally, the number of times of the scanning is determined in advance, and the scanning may be stopped irrespective of whether or not the resonant frequency has been detected.

According to the second embodiment described above, the frequency scanning condition is changed according to the number of times of the scanning, and thus it is possible to improve the oscillating capability of the device, shorten the time needed to scan for the resonant frequency, and finally shorten the time needed to treat the living tissue.

THIRD EMBODIMENT

Figure 9:
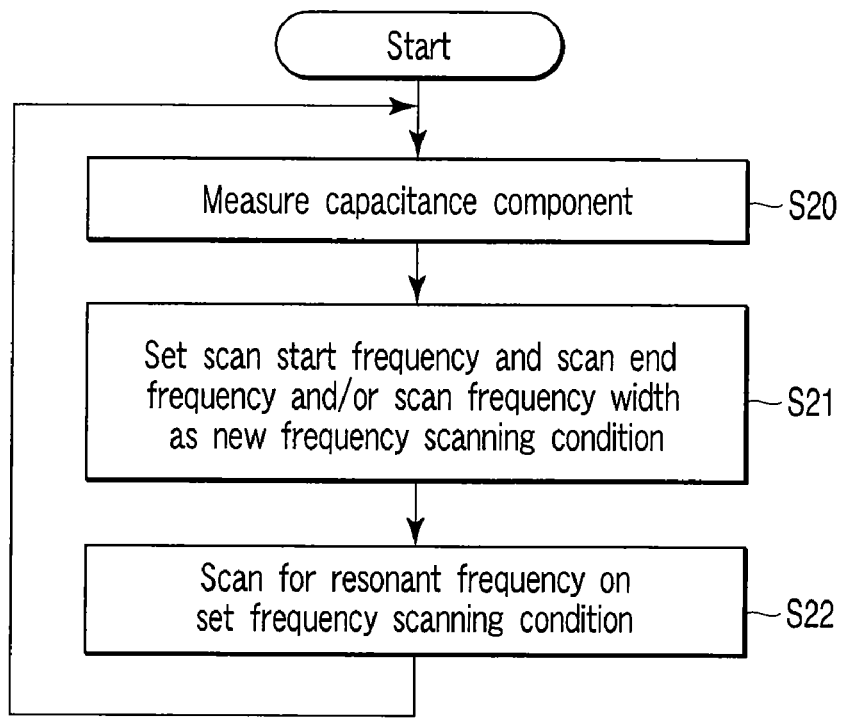
FIG. 9 is a flowchart for explaining a method of scanning for a resonant frequency of a hand-piece according to a third embodiment of the present invention.

FIG. 9 is a flowchart for explaining a method of scanning for a resonant frequency of a hand-piece according to a third embodiment of the present invention. The capacitance component of the hand-piece 2, specifically, the ultrasonic vibrator is varied depending on the type of the device and the use environment. If the capacitance component is varied, the characteristic curve of the impedance Z and the phase frequency characteristics of the voltage and the current described in connection with FIG. 6 are also varied. For example, when the capacitance component is large, fr and f2 become close to each other in the phase frequency characteristic as shown in FIG. 10(A). On the other hand, when the capacitance component is small, f1 and fr become close to each other in the phase frequency characteristic as shown in FIG. 10(B).

When fr and f2 are close to each other, if the scanning is started in search of the resonant frequency from the higher frequency side, the phase is abruptly changed between f2 and fr. Hence, if the scanning is performed in search of the resonant frequency slowly between f2 and fr, fr can be detected easier. On the other hand, even if the scanning is performed in search of the resonant frequency at a high speed between fr and f1, the oscillation capability of the device is not deteriorated. Conversely, when f1 and fr are close to each other, if the scanning is performed at a high speed from the start of the scanning on the higher frequency side to fr, and is performed slowly between fr and f1, the oscillation capability of the device is improved. That is, by changing the frequency scanning condition according to the capacitance component of the ultrasonic vibrator, the oscillation capability of the device can be improved.

First, the control circuit 1c measures the capacitance component of the ultrasonic vibrator (step S20). This capacitance component is measured by a known method on the basis of, for example, the phases of the voltage and the current detected from the drive signal supplied to the hand-piece 2, and the impedance. The control circuit 1c includes therein a table in which the capacitance component, scan start frequency, scan end frequency, and scan frequency width are made to correspond to each other. The control circuit 1c refers to this table to set at least one of (1) the scan start frequency and scan end frequency, and (2) the scan frequency width as a new frequency scanning condition (step S21). In terms of the example of FIG. 6, fs is the scan start frequency, fe is the scan end frequency, and fw is the scan frequency width. Here, fw is the interval between two sampling points.

Then, the control circuit 1c starts to scan for the resonant frequency on the set frequency scanning condition (step S22).

According to the third embodiment described above, the frequency scanning condition is changed according to the capacitance component of the hand-piece 2, specifically, the ultrasonic vibrator, and hence it is possible to perform frequency scanning suited for the type of the device or a change in the use environment, improve the oscillation capability of the device, shorten the time needed to scan for the resonant frequency, and ultimately shorten the time needed to treat the living tissue.

What is claimed is:

1. A power supply apparatus for operation for supplying a drive signal of a resonant frequency to a surgical instrument to drive the instrument comprising:
   a recognition section for recognizing a surgical instrument connected to the power supply apparatus;
   a setting section for setting a frequency scanning condition according to the surgical instrument recognized by the recognition section; and
   a scanning section for scanning for the resonant frequency of the surgical instrument on the basis of the frequency scanning condition set by the setting section.

2. The power supply apparatus for operation according to claim 1, wherein the frequency scanning condition includes at least one of (1) a scan start frequency and scan end frequency, and (2) a scan frequency width.

3. A power supply apparatus for operation for supplying a drive signal of a resonant frequency to a surgical instrument to drive the instrument comprising:
- a count section for counting the number of times the resonant frequency of the surgical instrument is scanned for;
- a setting section for setting a frequency scanning condition according to the number of times of the scanning counted by the count section; and
- a scanning section for scanning for the resonant frequency of the surgical instrument on the basis of the frequency scanning condition set by the setting section.

4. The power supply apparatus for operation according to claim 3, wherein the processing in the count section, the processing in the setting section, and the processing in the scanning section are repeatedly performed until the resonant frequency of the surgical instrument is detected.

5. The power supply apparatus for operation according to claim 3, wherein the frequency scanning condition includes at least one of (1) a scan start frequency and scan end frequency, and (2) a scan frequency width.

6. A power supply apparatus for operation for supplying a drive signal of a resonant frequency to a surgical instrument to drive the instrument comprising:
- a measurement section for measuring a capacitance component of the surgical instrument on the basis of a voltage, a current, and impedance detected from the drive signal supplied to the surgical instrument;
- a setting section for setting a frequency scanning condition according to the capacitance component measured by the measurement section; and
- a scanning section for scanning for the resonant frequency of the surgical instrument on the basis of the frequency scanning condition set by the setting section.

7. The power supply apparatus for operation according to claim 6, wherein the frequency scanning condition includes at least one of (1) a scan start frequency and scan end frequency, and (2) a scan frequency width.

8. A method of scanning for a resonant frequency of a surgical instrument by using a power supply apparatus for operation thereof, which apparatus includes: a recognition section for recognizing the surgical instrument; a setting section for setting a frequency scanning condition according to the surgical instrument recognized by the recognition section; and a scanning section for scanning for the resonant frequency of the surgical instrument on the basis of the frequency scanning condition set by the setting section, the method comprising:
- a recognition step of recognizing the surgical instrument in the recognition section;
- a setting step of setting a frequency scanning condition in the setting section according to the surgical instrument recognized in the recognition step; and
- a scanning step of scanning for the resonant frequency of the surgical instrument in the scanning section on the basis of the frequency scanning condition set in the setting step.

9. The method according to claim 8, wherein the frequency scanning condition includes at least one of (1) a scan start frequency and scan end frequency, and (2) a scan frequency width.

10. A method of scanning for a resonant frequency of a surgical instrument by using a power supply apparatus for operation thereof, which apparatus includes: a count section for counting the number of times the resonant frequency of the surgical instrument is scanned for; a setting section for setting a frequency scanning condition according to the number of times of the scanning counted by the count section; and a scanning section for scanning for the resonant frequency of the surgical instrument on the basis of the frequency scanning condition set by the setting section, the method comprising:
- a counting step of counting the number of times the resonant frequency of the surgical instrument is scanned for in the count section;
- a setting step of setting a frequency scanning condition in the setting section according to the number of times of the scanning counted in the counting step; and
- a scanning step of scanning for the resonant frequency of the surgical instrument in the scanning section on the basis of the frequency scanning condition set in the setting step.

11. The method according to claim 10, wherein the counting step, the setting step, and the scanning step are repeatedly performed until the resonant frequency of the surgical instrument is detected.

12. The method according to claim 10, wherein the frequency scanning condition includes at least one of (1) a scan start frequency and scan end frequency, and (2) a scan frequency width.

13. A method of scanning for a resonant frequency of a surgical instrument by using a power supply apparatus for operation thereof, which apparatus includes: a measurement section for measuring a capacitance component of the surgical instrument on the basis of a voltage, a current, and impedance detected from the drive signal supplied to the surgical instrument; a setting section for setting a frequency scanning condition according to the capacitance component measured by the measurement section; and a scanning section for scanning for the resonant frequency of the surgical instrument on the basis of the frequency scanning condition set by the setting section, the method comprising:
- a measurement step of measuring a capacitance component of the surgical instrument on the basis of a voltage, a current, and impedance detected from a drive signal supplied to the surgical instrument in the measurement section;
- a setting step of setting a frequency scanning condition in the setting section according to the capacitance component measured in the measurement step; and
- a scanning step of scanning for the resonant frequency of the surgical instrument in the scanning section on the basis of the frequency scanning condition set in the setting step.

14. The method according to claim 13, wherein the frequency scanning condition includes at least one of (1) a scan start frequency and scan end frequency, and (2) a scan frequency width.

* * * * *